(12) United States Patent
Boutet et al.

(10) Patent No.: US 8,825,141 B2
(45) Date of Patent: Sep. 2, 2014

(54) STERILE PROTECTIVE MEMBRANE WITH LIGHT GUIDES FOR A MEDICAL PROBE AND ASSOCIATED METHOD OF PRODUCTION

(75) Inventors: Jérôme Boutet, Claix (FR); Mathieu Debourdeau, Saint Pierre D'Allevard (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 38 days.

(21) Appl. No.: 13/281,107

(22) Filed: Oct. 25, 2011

(65) Prior Publication Data

US 2012/0108942 A1    May 3, 2012

(30) Foreign Application Priority Data

Oct. 27, 2010 (FR) ...................................... 10 58834

(51) Int. Cl.
*A61B 6/00* (2006.01)
(52) U.S. Cl.
USPC .......................................... 600/476; 600/473
(58) Field of Classification Search
USPC .................................................. 600/473–480
See application file for complete search history.

(56) References Cited

U.S. PATENT DOCUMENTS

| | | | |
|---|---|---|---|
| 4,870,952 A | 10/1989 | Martinez | |
| 5,283,722 A | 2/1994 | Koenen et al. | |
| 5,478,338 A | 12/1995 | Reynard | |
| 5,579,774 A * | 12/1996 | Miller et al. | 600/480 |
| 6,411,835 B1 * | 6/2002 | Modell et al. | 600/407 |
| 6,522,827 B1 * | 2/2003 | Loeb et al. | 385/147 |
| 6,826,422 B1 * | 11/2004 | Modell et al. | 600/407 |
| 2001/0041843 A1 * | 11/2001 | Modell et al. | 600/473 |
| 2002/0143275 A1 | 10/2002 | Sarvazyan et al. | |
| 2004/0186382 A1 * | 9/2004 | Modell et al. | 600/473 |
| 2006/0052709 A1 * | 3/2006 | DeBaryshe et al. | 600/476 |
| 2006/0253178 A1 * | 11/2006 | Masotti | 607/89 |
| 2008/0294056 A1 | 11/2008 | Boutet et al. | |
| 2009/0177094 A1 * | 7/2009 | Brown et al. | 600/476 |
| 2010/0010311 A1 * | 1/2010 | Miller et al. | 600/156 |
| 2010/0134607 A1 * | 6/2010 | Ishihara | 348/68 |
| 2010/0286791 A1 * | 11/2010 | Goldsmith | 623/23.7 |
| 2010/0292558 A1 * | 11/2010 | Saadat et al. | 600/407 |
| 2011/0261353 A1 * | 10/2011 | Teramura | 356/213 |
| 2012/0004577 A1 * | 1/2012 | Saadat et al. | 600/587 |
| 2012/0059366 A1 * | 3/2012 | Drews et al. | 606/33 |

OTHER PUBLICATIONS

Zhen Jiang, et al., "Trans-rectal Ultrasound-Coupled Near-Infrared Optical Tomography of the Prostate Part II: Experimental Demonstration", Optics Express, Oct. 27, 2008, pp. 17505-17520, vol. 16, NR. 22, Optical Society of America, US, XP002646498.

(Continued)

*Primary Examiner* — Sanjay Cattungal
(74) *Attorney, Agent, or Firm* — Baker & Hostetler LLP

(57) ABSTRACT

In the field of dual-mode medical probes, a simple device perfectly meets the double need for dual-modality and sterilization, and provides a sterile, disposable, or sterilizable protective membrane, also called a "glove" or "sock", equipped with optical fibers. This protective membrane can be slipped onto an ultrasound probe. It therefore ensures both the dual-mode functionality and perfect sterilization of the probe, this being the desired effect. The protective membrane is easy to produce and easy to use.

6 Claims, 3 Drawing Sheets

(56) References Cited

OTHER PUBLICATIONS

J. Masood et al.: "Condom perforation during transrectal ultrasound guided (TRUS) prostate biopsies: a potential infection risk," International Urology and Nephrology, vol. 39, 2007, pp. 1121-1124.

J. Boutet et al.: "Bimodal ultrasound and fluorescence approach for prostate cancer diagnosis," Journal of Biomedical Optics, vol. 14, 2009, pp. 064001-1 to 064001-7.

Z. Jiang et al.: "In vivo trans-rectal ultrasound-coupled optical tomography of a transmissible venereal tumor model in the canine pelvic canal," Journal of Biomedical Optics, vol. 14, May 2009.

W.W. Miller et al.: "Performance of an In-Vivo, Continuous Blood-Gas Monitor with Disposable Probe," Clinical Chemistry, vol. 33, No. 9, 1987.

C.C.Schulman: "Transrectal Prostatic Biopsy," International Urology and Nephrology, vol. 2, 1970, pp. 157-161.

\* cited by examiner

STERILE PROTECTIVE MEMBRANE WITH LIGHT GUIDES FOR A MEDICAL PROBE AND ASSOCIATED METHOD OF PRODUCTION

CROSS-REFERENCE TO RELATED APPLICATION

This application claims priority to foreign French patent application No. FR 1058834, filed on Oct. 27, 2010, the disclosure of which is incorporated by reference in its entirety.

FIELD OF THE INVENTION

The field of the invention is that of what are called multimode medical probes used in certain types of diagnosis. These probes combine the use of optical and ultrasound imaging.

BACKGROUND

Recently, what is known as multimode imaging, combining acquisition of various types of image, has experienced considerable growth in the medical diagnostic field. This is because it makes it possible to obtain both morphological and functional information. The first are obtained using X-ray or ultrasound probes and the second using positron emission tomography (PET) or magnetic resonance imaging (MRI) or using fluorescence imaging. In particular, the pairing of ultrasound/optical techniques seems particularly pertinent to certain applications such as mammography or the detection of anomalies in the prostate because these techniques are compatible in terms of cost, compactness and penetration depth.

Many research teams are currently developing instruments based on these two imaging modes, either for diagnostic applications or for phototherapy treatment applications.

At the present time, the main diagnostic tool for prostate cancer consists in carrying out several biopsies guided by and using an endorectal ultrasound probe. For the examination, the practitioner slips a sterile protective membrane around the probe reducing the risk of nosocomial infections. This protective membrane may be, depending on the practitioner, a simple condom or even a dedicated sterile glove. In France, each hospital follows its own procedure for sterilizing these probes.

However, during the ultrasound-guided biopsy protocol, the risk of the sterile protective membrane being perforated is about 9%. It is not negligible and leads to a risk of infection. The reader is referred to the study by J. Masood, S. Voulgaris, O. Awogu, C. Younis, A. J. Ball and T. W. Carr, "Condom perforation during transrectal ultrasound guided (TRUS) prostate biopsies: a potential infection risk," International Urology and Nephrology, Vol 39, 2007, p 1121-1124 for more information on this problem.

Furthermore, existing sterile gloves are not designed to be compatible with fluorescence measurements. In particular the following problems arise:
  dyes present in the material from which the protective membranes are made absorb some of the absorption and excitation light;
  the material from which the protective membrane is made may also induce a parasitic fluorescence signal in the wavelength range used; and
  the protective membrane may also, under certain conditions, deteriorate under the effect of laser light. Mention may be made, for example, of photoablation methods, which use a high-power laser to cut tissue.

Moreover, for several years sterilization criteria for tools used in medical environments have become more and more rigorous, thereby resulting in a tendency to use thicker, and therefore more light-absorbent, sterile gloves.

It is accepted at the present time that it is advantageous to use a probe which makes it possible to carry out both echography and fluorescence imaging, and some have chosen to develop dedicated devices, integrating an optical mode and acoustic echography in one and the same probe. Adding the optical mode is however liable to degrade the seal of the ultrasound part of the probe. This is because the presence of optical fibres protruding slightly from the surface of the probe may cause breaks in the seal of the whole device. Moreover, including optical fibres in an ultrasound probe represents a real technical challenge because these fibres have already been optimized for bulk. Such a modification implies completely reviewing current probe design and replacing existing probes, something that practitioners are loathe to do.

To solve the problems posed both by the dual-modality and sterilization of the probe, several solutions have been provided.

An American team proposed an ultrasonically and optically coupled probe for diagnosis of prostate cancer. The team was Z. Jiang, G. Holyoak, K. Bartels, J. Ritchey, G. Xu, C. Bunting, G. Slobodov and D. Piao, "In vivo trans-rectal ultrasound-coupled optical tomography of a transmissible venereal tumor model in the canine pelvic canal," JOURNAL OF BIOMEDICAL OPTICS, Vol 14, May 2009. However, this probe did not solve the problem of sterilization after use.

U.S. Pat. No. 5,283,722 of K. M. Peter and R. Trow, "Surgical-Type Glove and Illuminator Assembly" provided a sterile glove intended for a surgeon and equipped with a light source for illuminating the area of surgical work.

Another team proposed a fibre-coupled optical probe part of which was disposable, this probe was intended to measure certain properties of the blood, such as the pH, through a catheter. The reader is referred to the publication by W. W. Miller, M. Yafuso, C. F. Yan, H. K. Hui and S. Arick entitled "Performance of an in-vivo continuous blood-gas monitor with disposable probe" Clinical Chemistry, Vol 33, 1987, p 1538.

U.S. Pat. No. 4,870,952 of M. Martinez entitled "Fiber Optic Illuminator for Use in Surgery" describes a partially disposable optical probe for surgical applications.

It will also be noted that a Dutch team have proposed a disposable biopsy syringe for examining the prostate. The reader is referred to the publication by C. C. Schulman entitled "Transrectal prostatic biopsy" International Urology and Nephrology, Vol 2, 1970, p 157-161 on this subject.

SUMMARY OF THE INVENTION

None of these probes completely solves the problems faced. The object of the invention is to provide a simple device that meets perfectly the double need for dual-modality and sterilization. The device provided is a sterile, disposable, or sterilizable protective membrane, also called a "glove" or "sock", equipped with optical fibres. This protective membrane can be slipped onto an ultrasound probe. It therefore ensures both the dual-mode functionality and sterilization of the probe, this being the desired effect.

More precisely, the first subject of the invention is a sterile protective membrane for a medical probe, said protective membrane comprising a thin latex cap suitably shaped so as to completely protect the medical probe when used, characterized in that at least one optical fibre is included in said cap, said optical fibre comprising an optical coupling means at the free end of the cap, and the end being arranged so as to deliver light to or so as to receive light from the measurement region of the medical probe.

Advantageously, the optical fibres are plastic fibres, the latex is free from chromophores and the thickness of the latex of the cap is between 50 microns and 150 microns.

The second subject of the invention is a diagnostic instrument comprising a transrectal medical probe protected by a sterile protective membrane as defined above, said instrument comprising at least: an optical source arranged so as to address in sequence a first bundle of optical fibres, said first bundle being coupled, by means of an optical connection ring equipped with ferrules, to a first set of optical fibres included in the protective membrane; and optical collectors connected to a second bundle of optical fibres, said second bundle being coupled, by means of said optical connection ring, to a second set of optical fibres included in the protective membrane.

Advantageously, the medical probe is an endorectal probe or a vaginal echography probe.

Lastly, the third subject of the invention is the method for producing said sterile protective membrane; the method thus comprises the following steps:
  1st step: positioning optical fibres around a mould having the same shape as the ultrasound probe and holding these fibres in place using one or more flexible rings;
  2nd step: immersing the mould-fibres-rings assembly in a latex bath;
  3rd step: waiting for a film of latex to be deposited on the mould in the form of a gel; removing the mould-fibres-rings assembly from the latex bath; and leaving the latex coating to dry;
  4th step: if required, carrying out one or more additional dip coatings in order to increase the thickness of the latex coating; and
  5th step: once the desired latex thickness has been obtained, rolling up the open end of the recently moulded latex film so as to form a ring having a larger thickness.

BRIEF DESCRIPTION OF THE DRAWINGS

The invention will be better understood and other advantages will become clear on reading the following non-limiting description and by virtue of the appended figures among which.

DETAILED DESCRIPTION

The sterile protective membrane according to the invention makes it possible to deliver light from a source to the organ studied using an optical fibre called the excitation optical fibre, and to return detected fluorescence or scattered light to at least one detector using an optical fibre called the fluorescence or reception fibre. The protective membrane is made of a flexible and elastic material, allowing it to follow closely the shape of the endorectal probe used. Thus, it is possible to fit the protective membrane onto an existing acoustic endorectal probe easily.

The absorbance and parasitic signal levels generated by two commercially available, sterile latex protective membranes, used to protect transrectal probes, were measured following the experimental protocol described by J. Boutet, L. Herve, M. Debourdeau, L. Guyon, P. Peltie, J. M. Dinten, L. Saroul, F. Duboeuf and D. Vray, "Bimodal ultrasound and fluorescence approach for prostate cancer diagnosis," Journal of Biomedical Optics, Vol 14, 2009, p 064001, this protocol being described in paragraph 2. The presence of a sterile protective membrane representative of that found on the market was an addition to this protocol.

The material of the protective envelope must be thin and flexible. It must not comprise chromophores or fluorophores in a very high concentration, so as not to affect its optical transmission properties. The preferred material is latex, which meets these conditions, though it is still necessary to determine the optimal thickness: sufficiently thick to ensure a good tear resistance while being sufficiently thin to guarantee a good transmission of the optical signal, and a low emission level for the parasitic fluorescence signal. The expression "parasitic fluorescence signal" is understood to mean an optical signal produced by the material in response to excitation by light.

Figure 1:
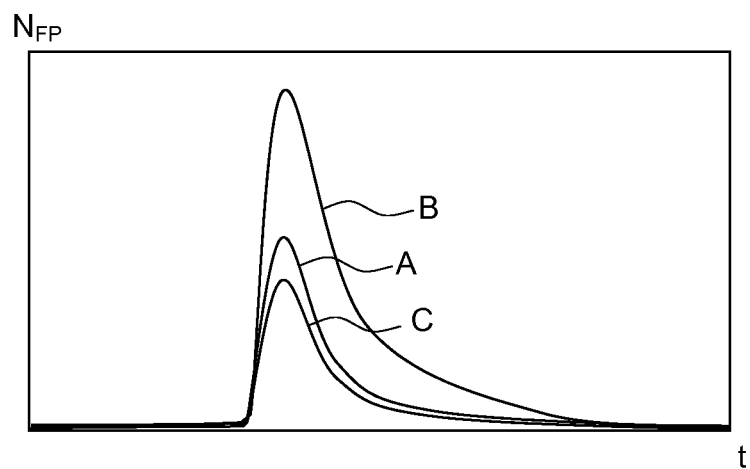
FIGS. 1 and 2 show the levels of parasitic fluorescence as a function of time generated by the chromophores present in a commercially available, sterile protective membrane and the transmission of a useful signal generated by a fluorescent inclusion through a sterile protective membrane.

The first parameter, illustrated in FIG. 1, shows the levels of parasitic fluorescence $N_{FP}$, as a function of time t, generated by the chromophores present in a commercially available, sterile, protective membrane in response to a short light pulse, i.e. the duration of which in general lay between 100 fs and 10 ps. Curve A shows the parasitic fluorescence generated by a thin protective membrane 100 μm in thickness and curve B shows the parasitic fluorescence generated by a thick protective membrane 500 μm in thickness. Finally, curve C shows the parasitic fluorescence signal generated by the environment in which the probe is immersed, obtained with the bare, unprotected probe. It is observed that the presence of a thick, sterile, protective membrane, i.e. having a thickness of about 500 μm, substantially increases the levels of parasitic fluorescence whereas the presence of a thin protective membrane, i.e. having a thickness of about 100 μm, does not substantially change these levels. During these tests, the probe is not placed near a fluorophore, so as to be certain that the signal measured is indeed an auto-fluorescence signal generated by the material, in this case latex. The experimental set-up used for these tests is similar to that shown in FIG. 4, except that the fluorescent inclusion 61 and the tissue phantom 60 were absent.

Figure 2:
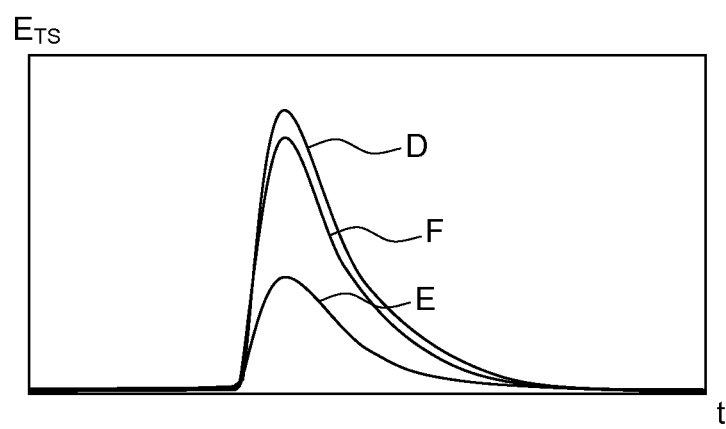

The second parameter, illustrated in FIG. 2, shows the intensity $E_{TS}$ of a useful signal coming from a fluorescent inclusion, representing a tumour marked by a fluorophore, this signal passing through a sterile protective membrane, in response to the same short light pulse employed in the preceding example. Curve D shows the intensity of the fluorescence signal as a function of time, through a thin protective membrane 100 μm in thickness and curve E shows the fluorescence intensity, as a function of time, through a thick protective membrane 500 μm in thickness. Finally, curve F shows the intensity of the fluorescence signal of the fluorescent inclusion, as a function of time, with no protective membrane. It is observed that the presence of a thick, sterile, protective membrane, i.e. having a thickness of about 500 μm, substantially reduces the intensity of the fluorescence signal, whereas the presence of a thin protective membrane leaves the intensity almost unchanged compared to the intensity of the fluorescence signal obtained with no protective membrane. The experimental set-up used during these tests is similar to that shown in FIG. 4, employing a fluorescent inclusion 61 near the probe.

Figure 3:
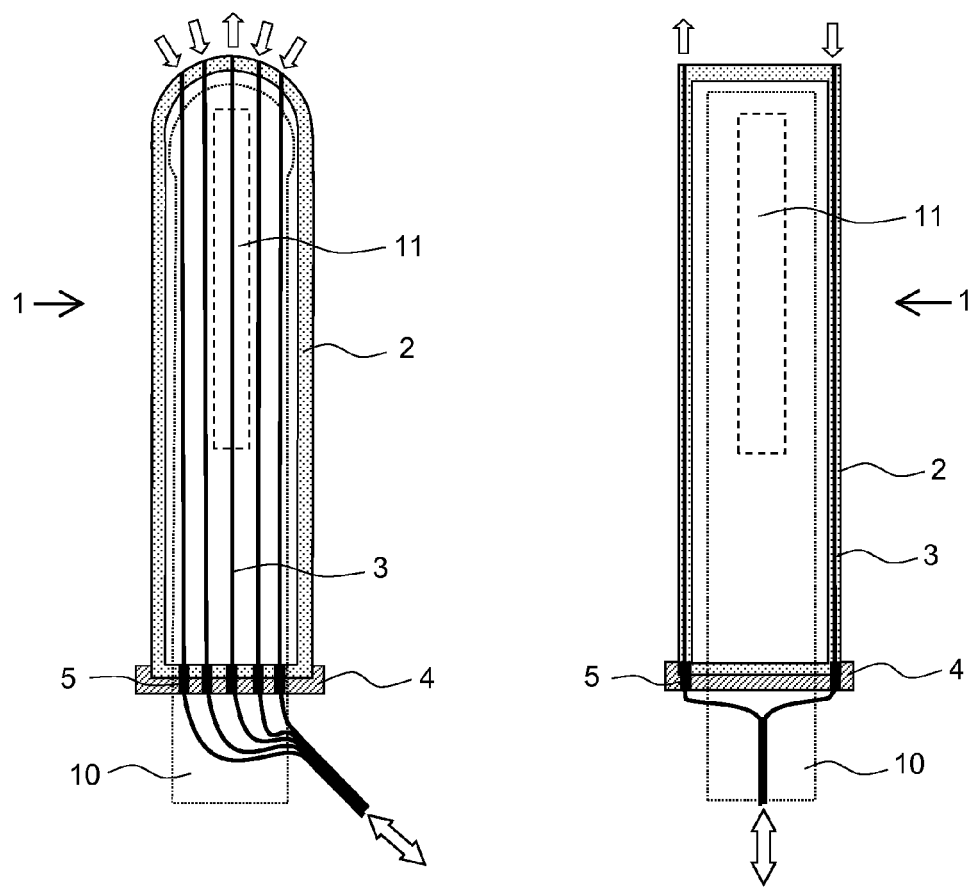
FIG. 3 shows a front view and a cross-sectional view of a sterile protective membrane according to the invention.

FIG. 3 shows a front view and a cross-sectional view of an exemplary sterile protective membrane 1 according to the invention. In order to ensure that the drawings are clear, the dimensions and thicknesses shown are not representative of the actual dimensions of the protective membrane. Also shown in these views, drawn with dotted and dashed lines, are the protected ultrasound probe 10 and its ultrasound transducer 11.

The protective membrane comprises a rectangular latex cap 2 and optical fibres 3 included in the latex film which emit light coming from an external source (not shown in FIG. 3) and receive light emitted by the biological tissue in response to the excitation light. The path taken by the light in the protective membrane is indicated by thick white arrows in FIG. 3. Preferably, the excitation and reception fibres are separate. It is thus possible to independently optimize the excitation and reception pathways. The fibres are connected to an optical connection ring 4 equipped with ferrules 5. This ring is independent of the protective membrane 1 and may be detached therefrom.

Typical dimensions for the sterile protective membrane according to the invention are a diameter of about 2 centimeters and a length of about 15 centimeters.

It is preferable for the latex film to have a small thickness of about 100 microns so as to reduce the levels of parasitic fluorescence and to increase transmission of the useful signal, as was described above relative to FIGS. 1 and 2. A good compromise is for the film to have a thickness of between 50 and 150 microns, this thickness range also providing a good perforation resistance. Preferably, materials such as nitrile or polyurethane are not used because their high chromophore content is liable to interfere with the final measurement. The latex is either natural or synthetic, natural latex being less likely to tear.

The length of the optical fibres of course depends on the size of the probe to be protected. Normally, the length of the optical fibres will be about 20 centimeters.

The emission or excitation fibres may have a polyimide cladding and a silica core. By way of example, the various geometric parameters may be:
core diameter: 62.5 microns;
cladding diameter: 155 microns;
numerical aperture: 0.27; and
minimum radius of curvature: 17 millimeters.

The reception fibres may be plastic fibres. These fibres have many advantages. They are flexible and have a high numerical aperture, about 0.5, making it possible to collect a high light flux. By way of example, the various geometrical parameters may be:
core diameter: 1 millimeter;
numerical aperture: 0.46; and
minimum radius of curvature: 10 millimeters.

The number of excitation and reception fibres depends on the application envisaged. The higher the number of detection fibres, the better the resolution. In practice, the number of fibres is limited to a few units, and varies generally between 2 and 20.

By way of example, the method for producing the protective membrane according to the invention comprises the following steps:
1st step: positioning optical fibres around a mould having the same shape as the ultrasound probe used and holding these fibres in place using one or more flexible rings;
2nd step: immersing the mould-fibres-rings assembly in a latex bath;
3rd step: waiting for a film of latex to be deposited on the mould in the form of a gel; removing the mould-fibres-rings assembly from the latex bath; and leaving the latex coating to dry;
4th step: if required, carrying out one or more additional dip coatings in order to increase the thickness of the latex coating; and
5th step: once the desired latex thickness has been obtained, rolling up the open end of the recently moulded latex film so as to form a ring having a larger thickness.

The way in which the protective membrane according to the invention is used is very simple. It comprises the following steps:
1st step: sliding the optical ring around the transrectal ultrasound probe;
2nd step: taking a sterile protective membrane out of its sterile packaging;
3rd step: sliding the protective membrane over the transrectal ultrasound probe;
4th step: connecting the fibres of the protective membrane to those of the ring, the latter preferably comprising a mechanical poka-yoke or visual markings;
5th step: carrying out the dual-mode, optical and ultrasound, examination of the patient;
6th step: after the examination, disconnecting the fibres of the protective membrane from the optical ring;
7th step: removing the protective membrane and disposing of it; and
8th step: removing the optical ring from the ultrasound probe.

In a variant, the protective membrane may be reusable. It is then necessary for it to consist of elements able to withstand treatment in an autoclave for sterilization.

Figure 4:
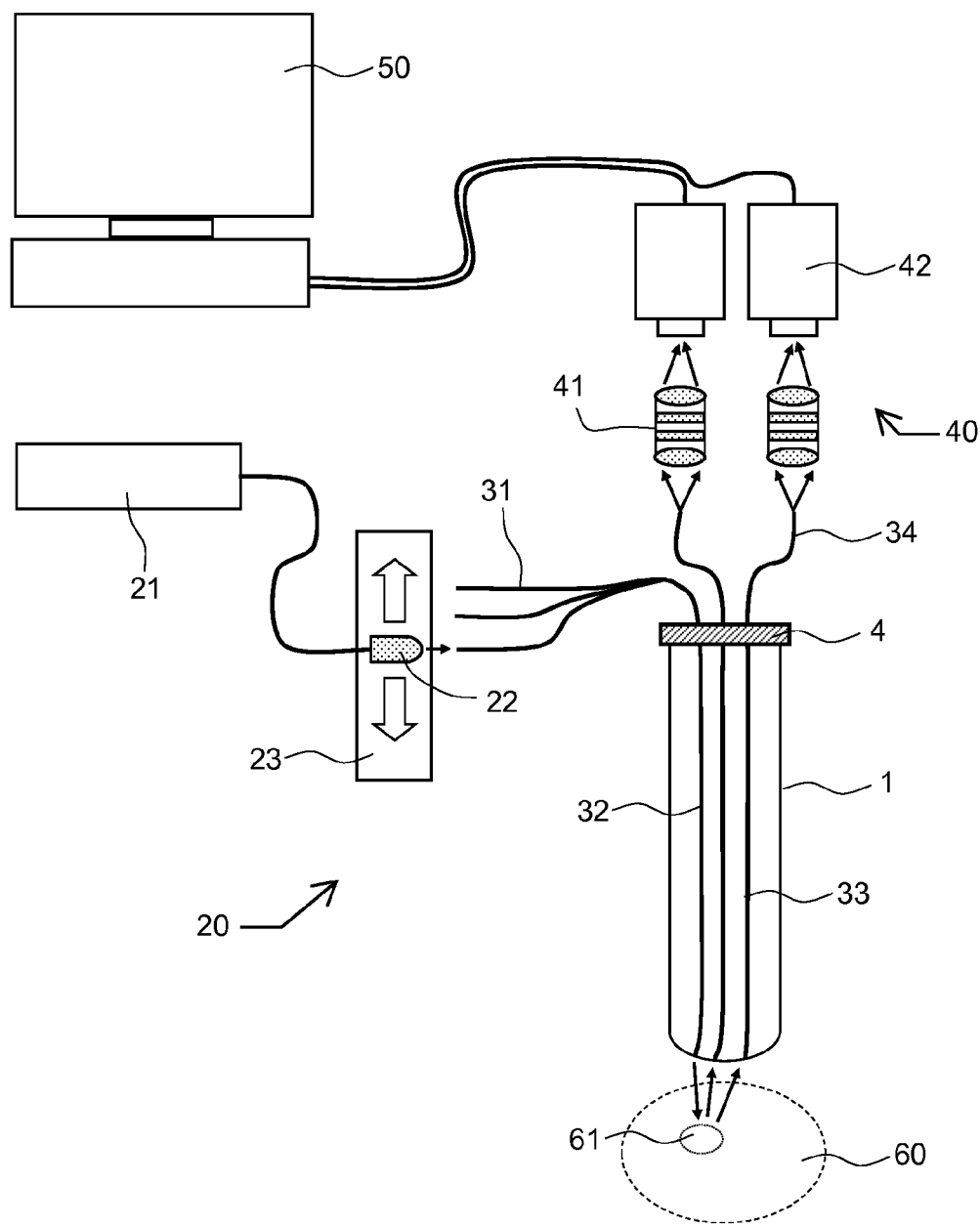
FIG. 4 shows an analysis or diagnostic instrument comprising a medical probe of the transrectal type, the probe being protected by a sterile protective membrane according to the invention.

By way of example, FIG. 4 shows an analysis or diagnostic instrument comprising a medical probe protected by a sterile protective membrane according to the invention. By way of example, the probe may be an endorectal probe or a vaginal echography probe. It may, of course, be used for analysis of other natural cavities.

Only the optical part 20 of this instrument is shown in FIG. 4. It comprises:
a pulsed or continuous optical source 21 arranged so as to address in sequence a first bundle 31 of optical fibres belonging to the sterile protective membrane 1, said first bundle 31 being coupled, by means of the optical connection ring 4, equipped with ferrules, to a first set of emission optical fibres 32 included in the protective membrane 1. In the case of FIG. 4, the sequential sweeping is obtained by means of an optical coupling device 22 mounted on translation means 23. Other optical systems are possible. In the experimental set-up used by the inventors, the light source 21 was a pulsed titanium-sapphire laser, producing 50 femtosecond pulses at 770 nm with a frequency of 80 MHz. The average power was 10 mW. The light emitted was filtered using a pass-band filter centred on the wavelength of 770 nm. The optical coupling device 22 was a 10× magnification lens mounted on a moving plate 23; and
optical collectors 40 connected to a second bundle 34 of optical fibres, said second bundle being coupled, by means of the optical connection ring 4, to a second set of reception optical fibres 33 included in the protective membrane 1. Generally, the collectors 40 comprise an optical assembly 41, optionally equipped with optical filters and a photosensitive device 42. The optical assembly 41 may for example comprise a 6.3× magnification lens and optical filters, notably making it possible to remove the wavelengths of the excitation light. The photosensitive device 42 may be a light-intensified high-speed camera. All the information generated by the various optical collectors is processed and displayed by dedicated data-processing means 50.

The light from the fibres is emitted towards the biological tissues inspected or phantoms simulating these tissues 60, these tissues emitting, in response, light called back-scattered light, the analysis of which makes it possible to obtain information about whether lesions or tumours 61 are present. During experimental tests carried out on a phantom, the tumour was simulated by a fluorescent inclusion that was placed in the phantom. The back-scattered light was for example fluorescence light generated by fluorescent markers previously introduced.

This protective membrane is noteworthy in that it is made exclusively of inexpensive elements, allowing it to be used just once, the protective membrane being no more than a simple, disposable consumable.

The advantages of a protective membrane according to the invention are:
- optimized hygiene;
- a complicated disinfection procedure is no longer required;
- the protective membrane is compatible with existing ranges of ultrasound probes, i.e. practitioners do not need to buy a specific dual-mode probe;
- the reproducibility of the optical measurement is optimized, i.e. at the start of the examination the interface of the optical surfaces is perfectly clean; and
- the optical coupling is improved since the fibres make direct contact with the human tissues, the latex film of the protective membrane no longer interferes with the measurement.

The invention claimed is:

1. A flexible sterile protective membrane for a medical probe, comprising:
   a thin latex cap shaped to completely protect the medical probe when used, wherein a thickness of the latex of the cap is between 50 microns and 150 microns,
   wherein at least one optical fibre is included in a thickness of said cap, said at least one optical fibre comprising an optical coupling means at a free end of the cap, the free end being arranged to deliver light to or receive light from a measurement region of the medical probe.

2. The sterile protective membrane for a medical probe according to claim 1, wherein the at least one optical fibre is a plastic fibre.

3. The sterile protective membrane for a medical probe according to claim 1, wherein the optical coupling means is configured to optically connect said at least one optical fibre to a light source or to a light detector.

4. An analysis or diagnostic instrument comprising a medical probe protected by a sterile protective membrane according to claim 1, wherein said instrument further comprises:
   an optical source arranged to address in sequence a first bundle of optical fibres, said first bundle of optical fibres being coupled, by means of an optical connection ring equipped with ferrules, to a first set of optical fibres included in the protective membrane; and
   optical collectors connected to a second bundle of optical fibres, said second bundle of optical fibres being coupled, by means of said optical connection ring, to a second set of optical fibres included in the protective membrane.

5. An analysis or diagnostic instrument according to claim 4, wherein the medical probe is an endorectal probe or a vaginal echography probe.

6. A method of producing a sterile protective membrane according to claim 1, comprising:
   positioning optical fibres around a mould having a same shape as the medical probe and holding the optical fibres in place using one or more flexible rings;
   immersing an assembly of the mould, the optical fibers, and the one or more flexible rings in a latex bath;
   waiting for a film of latex to be deposited on the mould in the form of a gel, removing the assembly from the latex bath; and leaving the latex coating to dry;
   if required, carrying out one or more additional dip coatings in order to increase the thickness of the latex coating; and
   once the desired latex thickness has been obtained, rolling up an open end of the recently moulded latex film so as to form a ring having a thickness larger than the thickness of the latex film.

* * * * *